(12) United States Patent
Rioux et al.

(10) Patent No.: US 6,972,040 B2
(45) Date of Patent: Dec. 6, 2005

(54) DRAINING BODILY FLUID

(75) Inventors: Robert F. Rioux, Ashland, MA (US); Christopher R. O'Keefe, Holliston, MA (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 68 days.

(21) Appl. No.: 10/299,927

(22) Filed: Nov. 19, 2002

(65) Prior Publication Data
US 2003/0073978 A1   Apr. 17, 2003

Related U.S. Application Data

(63) Continuation of application No. 09/858,789, filed on May 16, 2001, now Pat. No. 6,494,855.

(51) Int. Cl.[7] .............................................. A61F 2/04
(52) U.S. Cl. ............................... 623/23.66; 623/23.65; 604/8
(58) Field of Search .................... 604/8, 9; 623/23.64, 623/23.65, 2.37, 0.66

(56) References Cited

U.S. PATENT DOCUMENTS

| | | |
|---|---|---|
| 3,731,670 A | 5/1973 | Loe |
| 3,783,454 A | 1/1974 | Sausse et al. |
| 3,938,529 A | 2/1976 | Gibbons |
| 3,995,642 A | 12/1976 | Adair |
| 4,212,304 A | 7/1980 | Finney |
| 4,225,979 A | 10/1980 | Rey et al. |
| 4,284,081 A | 8/1981 | Kasper et al. |
| 4,307,723 A | 12/1981 | Finney |
| 4,334,327 A | 6/1982 | Lyman et al. |
| 4,350,161 A | 9/1982 | Davis, Jr. |
| 4,432,757 A | 2/1984 | Davis, Jr. |
| 4,501,580 A | 2/1985 | Glassman |
| 4,531,933 A | 7/1985 | Norton et al. |
| 4,551,137 A | 11/1985 | Osborne |
| 4,610,657 A | 9/1986 | Densow |
| 4,671,795 A | 6/1987 | Mulchin |
| 4,813,429 A | 3/1989 | Eshel et al. |
| 4,813,925 A | 3/1989 | Anderson, Jr. et al. |
| 4,813,935 A | 3/1989 | Haber et al. |
| 4,820,262 A | 4/1989 | Finney |
| 4,874,360 A | 10/1989 | Goldberg et al. |
| 4,931,037 A | 6/1990 | Wetterman |

(Continued)

FOREIGN PATENT DOCUMENTS

DE        295 07 519        9/1995

(Continued)

OTHER PUBLICATIONS

Hepperlen et al., "Self-Retained Internal Ureteral Stents: A New Approach," The Journal of Urology, Jun. 1978, vol. 119 (pp. 731-734).

(Continued)

Primary Examiner—Bruce E. Snow
(74) Attorney, Agent, or Firm—Edwards & Angell, LLP

(57) ABSTRACT

A urethral prosthesis with prostatic and bulbar segments connected by two types of ties allows the prosthesis to assume at least two configurations different with inter-segmental distances adapted to situations where the patient either has or does not have normal control of the external sphincter. This is particularly useful for a patient undergoing an anesthetic procedure that affects the external sphincter muscles. When the muscles are anesthetized, the prosthesis may provide constant urine voiding, and when the anesthetic effects wear off, the prosthesis may assume a different configuration to allow the sphincter to reassert control over urinary voiding.

21 Claims, 7 Drawing Sheets

U.S. PATENT DOCUMENTS

| | | |
|---|---|---|
| 4,932,938 A | 6/1990 | Goldberg et al. |
| 4,932,956 A | 6/1990 | Reddy et al. |
| 4,946,449 A | 8/1990 | Davis, Jr. |
| 4,954,126 A | 9/1990 | Wallsten |
| 4,957,479 A | 9/1990 | Roemer |
| 4,969,474 A | 11/1990 | Schwarz |
| 4,973,301 A | 11/1990 | Nissenkorn |
| 4,976,735 A | 12/1990 | Griffith et al. |
| 4,990,133 A | 2/1991 | Solazzo |
| 4,994,019 A | 2/1991 | Fernandez et al. |
| 5,004,454 A | 4/1991 | Beyar et al. |
| 5,007,898 A | 4/1991 | Rosenbluth et al. |
| 5,012,822 A | 5/1991 | Schwarz |
| 5,019,102 A | 5/1991 | Hoene |
| 5,030,227 A | 7/1991 | Rosenbluth |
| 5,041,092 A | 8/1991 | Barwick |
| 5,085,664 A | 2/1992 | Bozzo |
| 5,096,454 A | 3/1992 | Samples |
| 5,097,848 A | 3/1992 | Schwarz |
| 5,112,306 A | 5/1992 | Burton et al. |
| 5,116,309 A | 5/1992 | Coll |
| 5,140,999 A | 8/1992 | Ardito |
| 5,141,502 A | 8/1992 | Macaluso, Jr. |
| 5,147,370 A | 9/1992 | McNamara et al. |
| 5,176,626 A | 1/1993 | Soehendra |
| 5,176,664 A | 1/1993 | Weisman |
| 5,213,575 A | 5/1993 | Scotti |
| 5,224,953 A | 7/1993 | Morgentaler |
| 5,246,445 A | 9/1993 | Yachia et al. |
| 5,269,802 A | 12/1993 | Garber |
| 5,282,472 A | 2/1994 | Companion et al. |
| 5,312,430 A | 5/1994 | Rosenbluth et al. |
| 5,322,501 A | 6/1994 | Mahmud-Durrani |
| 5,344,435 A | 9/1994 | Turner et al. |
| 5,346,467 A | 9/1994 | Coll |
| 5,354,263 A | 10/1994 | Coll |
| 5,366,506 A | 11/1994 | Davis |
| 5,380,268 A | 1/1995 | Wheeler |
| 5,391,196 A | 2/1995 | Devonec |
| 5,401,257 A | 3/1995 | Chevalier, Jr. et al. |
| 5,466,242 A | 11/1995 | Mori |
| 5,490,521 A | 2/1996 | Davis et al. |
| 5,512,032 A | 4/1996 | Kulisz et al. |
| 5,514,176 A | 5/1996 | Bosley, Jr. |
| 5,514,178 A | 5/1996 | Torchio |
| 5,518,498 A | 5/1996 | Lindeberg et al. |
| 5,525,388 A | 6/1996 | Wand et al. |
| 5,527,281 A | 6/1996 | Haas |
| 5,527,336 A | 6/1996 | Rosenbluth et al. |
| 5,569,219 A | 10/1996 | Hakki et al. |
| 5,599,291 A | 2/1997 | Balbierz et al. |
| 5,601,537 A | 2/1997 | Frassica |
| 5,609,583 A | 3/1997 | Hakki et al. |
| 5,624,374 A | 4/1997 | Von Iderstein |
| 5,624,410 A | 4/1997 | Tsukada et al. |
| 5,647,843 A | 7/1997 | Mesrobian et al. |
| 5,667,486 A | 9/1997 | Mikulich et al. |
| 5,681,274 A | 10/1997 | Perkins et al. |
| 5,684,051 A | 11/1997 | Thompson |
| 5,711,314 A | 1/1998 | Ardito |
| 5,713,877 A | 2/1998 | Davis |
| 5,752,971 A | 5/1998 | Rosenbluth et al. |
| 5,766,209 A | 6/1998 | Devonec |
| 5,776,161 A | 7/1998 | Globerman |
| 5,782,838 A | 7/1998 | Beyar et al. |
| 5,782,916 A | 7/1998 | Pintaauro et al. |
| 5,792,400 A | 8/1998 | Talja et al. |
| 5,795,319 A | 8/1998 | Ali |
| 5,814,006 A | 9/1998 | Planz |
| 5,820,554 A | 10/1998 | Davis et al. |
| 5,830,179 A | 11/1998 | Mikus et al. |
| 5,865,815 A | 2/1999 | Tihon |
| 5,876,417 A | 3/1999 | Devonec et al. |
| 5,906,575 A | 5/1999 | Conway et al. |
| 5,911,732 A | 6/1999 | Hojeibane |
| 5,916,195 A | 6/1999 | Eshel et al. |
| 5,928,217 A | 7/1999 | Mikus et al. |
| 5,931,860 A | 8/1999 | Reid et al. |
| 5,964,744 A | 10/1999 | Balbierz et al. |
| 5,964,771 A | 10/1999 | Beyar et al. |
| 6,004,348 A | 12/1999 | Banas et al. |
| 6,013,102 A | 1/2000 | Pintauro et al. |
| 6,022,312 A | 2/2000 | Chaussy et al. |
| 6,033,413 A | 3/2000 | Mikus et al. |
| 6,056,775 A | 5/2000 | Borghi et al. |
| 6,059,808 A | 5/2000 | Boussignac et al. |
| 6,063,113 A | 5/2000 | Kavteladze et al. |
| 6,066,168 A | 5/2000 | Lau et al. |
| 6,139,536 A | 10/2000 | Mikus et al. |
| 6,162,377 A | 12/2000 | Ghosh et al. |
| 6,494,855 B2 * | 12/2002 | Rioux et al. .................. 602/67 |
| 6,494,879 B2 * | 12/2002 | Lennox et al. ................. 606/8 |
| 2003/0069636 A1 * | 4/2003 | Solem et al. ............... 623/2.37 |

FOREIGN PATENT DOCUMENTS

| | | |
|---|---|---|
| EP | 0 808 611 | 11/1997 |
| EP | 0 862 898 | 9/1998 |
| WO | WO 94/18907 | 1/1994 |
| WO | WO 96/02210 A1 | 2/1996 |
| WO | WO 00/21462 | 4/2000 |

OTHER PUBLICATIONS

Collier et al., "Proximal Stent Displacement as Complication of Pigtail Ureteral Stent," Urology, Apr. 1979, vol. XIII, No. 4 (pp. 372-375).

Mardis et al., "Polyethylene Double-Pigtail Ureteral Stents," Urologic Clinics of North America, Feb. 1982, vol. 9, No. 1 (pp. 95-101).

Copy of International Search Report PCT/US02/13656.

* cited by examiner

DRAINING BODILY FLUID

CROSS-REFERENCE TO RELATED APPLICATION

This is a continuation of and claims priority to a prior U.S. patent application Ser. No. 09/858,789, filed on May 16, 2001 now U.S. Pat. No. 6,494,855.

TECHNICAL FIELD

The invention generally involves urethral prostheses and related methods for draining bodily fluid from a patient.

BACKGROUND INFORMATION

Normal voiding of urine can be controlled through a patient's sphincter muscles, including voluntary control through the external sphincter. When functions of sphincter muscles are temporarily compromised, for example, due to anesthesia, a patient's control over normal urine voiding is likewise temporarily compromised.

Medical professionals that treat patients undergoing an anesthetic procedure currently have limited options for addressing urinary retention during and after the procedure. These include the use of a Foley catheter. In many cases, because post-operation assistance in voiding is needed (such as in the case of a urethral stenosis), the Foley catheter will remain in the patient's urethra. However, there are disadvantages in the use of a Foley catheter after an anesthetic procedure. For example, because the Foley catheter provides constant drainage through the urethra by maintaining the internal sphincter open, it does not allow the patient to control voiding even after the patient recovers normal sphincter function. This has brought inconvenience and emotional distress to the patient. Also, the Foley catheter extends outside the body, again causing the patient emotional distress and discomfort. The extracorporeal portion of the Foley catheter also subjects the patient to risks of infection.

SUMMARY OF THE INVENTION

It is an object of the invention to provide a patient (e.g., a human male) with assisted urinary voiding, while also allowing the patient to control the external sphincter muscle as it regains functionality, such as after an anesthetic procedure. It is another object of the invention to provide the patient with such assisted and controllable release without the discomfort, emotional distress, or infection rates associated with conventional treatments.

In one aspect, the invention relates to a urethral prosthesis capable of adopting at least two configurations depending on the functioning or non-functioning of a patient's external sphincter muscles. When the external sphincter muscles are not functioning or malfunctioning, the prosthesis may assume a compact configuration (locked or tied), and be placed in the urethra and adjacent the external sphincter muscles to provide constant drainage. When the external sphincter regains its function, the prosthesis may be transformed into an extended configuration. Reconfiguration will allow reposition of portions of the prosthesis away from the external sphincter muscles so that the muscles can contract and control urinary voiding.

An embodiment in accordance with these aspects of the invention includes a first segment, a second segment, and an adjustable tie connecting the two segments. The first segment includes a distal portion with at least one distal opening for receiving fluids such as urine, and a proximal portion with at least one proximal opening. A lumen extends from the at least one distal opening to the at least one proximal opening. The second segment similarly includes a distal portion, a proximal portion, and a lumen extending from at least one distal opening to at least one proximal opening. The connecting tie is adjustable with a variety of inter-segmental lengths; such adjustments result in a variety of corresponding distances between the segments. The tie may be adjusted to shorten the distance between the segments so that the proximal portion of the first segment directly contacts the distal portion of the second segment. This "compact" configuration of the prosthesis is useful when patient's external sphincter is malfunctioning because the sphincter muscles may be held open by the prosthesis, resulting in constant drainage. When the external sphincter regains its function and voluntary control over the assisted voiding is desired, the prosthesis can be adjusted to assume an "extended" configuration. To do so, the inter-segmental distance is lengthened to allow insertion of an object, such as a portion of the external sphincter, which intercepts fluid communication between the lumens of the two segments. Under this extended configuration, the prosthesis permits functional sphincter muscles to contract and block, or extend and open fluid communication between the lumens, and therefore, achieving voluntary control over assisted urine voiding.

The adjustable tie in this embodiment may comprise a thread with two-ends. The ends may be connected or unconnected. In a preferred embodiment, the thread forms at least one loop between the proximal portion of the first segment and the distal portion of the second segment. In a particularly preferred embodiment, the thread forms a one-and-a half loop between the segments. The ends of the thread may be knotted together. Upon pulling the knot in a substantially proximal direction, the tie tightens the connection between the two segments, i.e., it shortens the inter-segmental distance.

The prosthesis, in accordance with another aspect of the invention, may further include a second tie connecting the proximal portion of the first segment and the distal portion of the second segment. This second tie has a pre-determined inter-segmental length between the first and the second segments of the prosthesis. The pre-determined inter-segmental length in turn sets the maximum value for the distance between the first and the second segments of the prosthesis. Such a maximum inter-segmental distance may be sufficient for the insertion of at least a portion of the functional external sphincter to effect voluntary control over fluid drainage. To reach this maximum inter-segmental distance, a retrieval piece may be connected to the proximal portion of the second segment. This retrieval piece may be a thread that can be pulled upon to help adjust the distance between the prosthetic segments, e.g., by pulling substantially away from the first prosthetic segment. Furthermore, a third segment may be removably connected to the proximal portion of the second segment. The third segment includes a distal portion, a proximal portion, and a lumen extending from at least one distal opening to at least one proximal opening. Fluid flowing from the lumens of the first and second segment can be relayed through the lumen of the third segment and emptied into a drainage bag connected to the proximal portion of the third segment.

An embodiment according to another aspect of the invention includes a first and a second segments similar to the ones described above. At least two ties connect the segments. The first tie engages the two segments by holding the two segments close enough to allow fluid communication between the lumens of the segments. In a preferred embodiment, the first tie holds the proximal portion of the first segment in direct contact with the distal portion of the second segment. The second tie connects the two prosthetic segments together at an inter-segmental distance upon disengagement of the first tie. This inter-segmental distance may be long enough to permit bodily control of fluid communication between the tubular lumens (e.g., insertion of portions of a sphincter muscle). Again, a retrieval piece may be connected to the proximal portion of the second segment. This retrieval piece may be a thread that can be pulled upon to help increase the distance between the prosthetic segments. Furthermore, a third segment with a lumen may be removably connected to the proximal portion of the second segment. Again, fluid flowing from the lumens of the first and second segment can be relayed through the lumen of the third segment and emptied into a further connected drainage bag.

Embodiments of the invention may include additional features. For instance, the first segment may incorporate an inflatable balloon. The balloon may be used for proper placement of the prosthesis. The distal portion of the first segment may further comprise a coudé tip. The first and second tubular segments are preferably made of a biocompatible material, such as silicone.

A method is provided for draining bodily fluid from a patient. A prosthesis having two connected segments is inserted into the urethra of a patient, then the distance between the segments is adjusted in response to sphincter functionality. When the patient has temporarily lost his sphincter function, the distance between the two segments may be shortened to allow fluid communication between the lumens of the prosthetic segments. When the patient regains sphincter function, the two segments of the prosthesis can be adjusted further apart to allow the sphincter muscles to come in between the two segments. A prosthesis with an adjustable tie as described above is useful for these purposes. The prosthesis may include a retrieval piece connected to the second segment. Pulling the retrieval piece substantially away from the first segment may help lengthen the inter-segmental distance, while pulling both ends of the adjustable tie shortens the inter-segmental distance. Furthermore, a second tie may be also provided to connect the proximal portion of the first segment with the distal portion of the second segment. The second tie connects the two segments at a distance from each other, limited by a pre-determined length. This pre-determined inter-segmental distance may be long enough to allow the patient's sphincter muscles to come in between the two segments and control voiding.

Another method is provided for draining bodily fluid from a patient. A prosthesis having two segments is inserted into the urethra of a patient, and the two segments are connected by at least two ties. The first tie engages the two segments by holding the two segments close enough to allow fluid communication between the lumens of the segments. The second tie has a longer inter-segmental length. When the first tie is engaged, constant drainage is provided. However, when sphincter control over urine voiding is desired, the first tie is disengaged from the prosthesis and/or removed from the urethra while at least a portion of the prosthesis remains in the urethra. And the second segment may be pulled away from the first segment through a retrieval piece attached to the second segment, increasing the inter-segmental distance. Because the first tie is disengaged, only the second tie is holding the tubular segments together, and its inter-segmen-tal length determines the distance between the prosthetic segments. This distance may be long enough for the sphincter muscles to assert control over fluid communication between the lumens.

The foregoing and other objects, aspects, features, and advantages of the invention will become more apparent from the following description including drawings and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

The invention involves a urethral prosthesis for providing relief of urinary retention, and to related methods. Specifically, the invention provides devices and methods for assisting urinary release under different physiological conditions, namely, the functioning or nonfunctioning of a patient's sphincter muscles in relation to controlling urinary release. The invention provides prostheses that each has at least two configurations adapted for the different conditions of the sphincter muscles.

Figure 1:
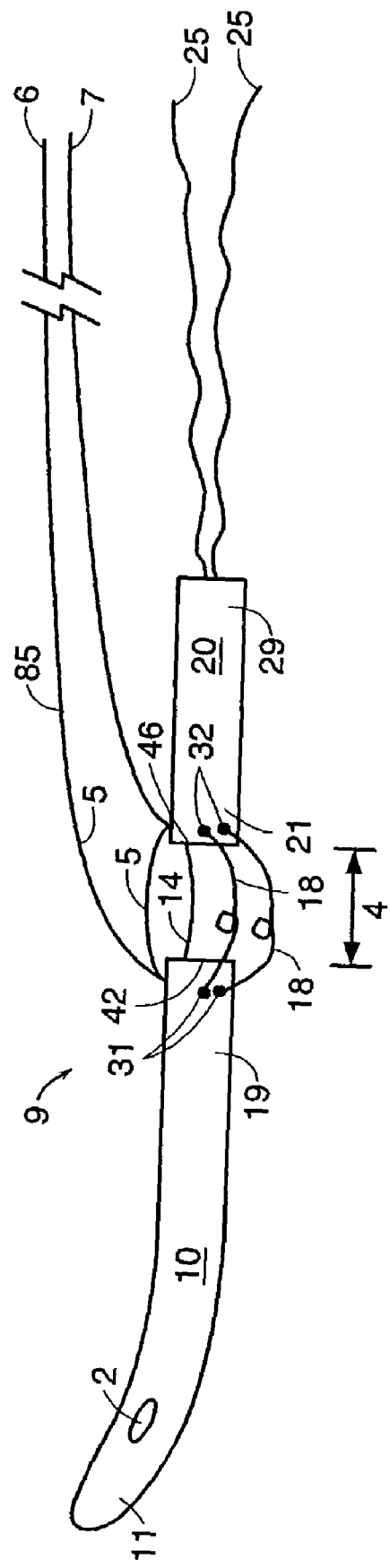
FIG. 1 is a schematic view of one embodiment of a prosthesis according to the invention.

An embodiment of a urethral prosthesis of the invention for use in treating urinary retention is illustrated in FIG. 1. A prosthesis 9 includes a first segment 10 and a second segment 20, connected by at least one adjustable tie 5. Both segments may assume a variety of shapes, such as cylindrical, conical, or a combination of various shapes, formed by an outer surface and a lumen surface that may be smooth, ridged or pleated. The segments may have cross sections that are of any shape capable of maintaining an orifice open, including but not limited to the following geometric forms: circular, oval, elliptical, or crescent. Each segment's cross section may further change through its length in terms of size or shape. The segments 10 and 20 may be composed of any biocompatible material, such as silicone, PTFE, polyurethane, and so on. The first tubular segment 10 has a distal portion 11 and a proximal portion 19, and is sometimes termed the "prostatic segment" as it is designed to reside in the prostatic section of the urethra when placed properly in the urethra. The distal direction, as used in this application, is from the perspective of an operator, and therefore, when the prosthesis is inserted into the urethra of a patient, its distal portion points into the patient's body. The distal portion 11 of the first segment 10 may be straight, rounded, or may assume the shape of a coudé tip (a closed and curved tip, e.g., with a bent of about 40 degree angle) for ease of placement inside the urethra. A coudé tip is well known in the art, and is described in literatures such as U.S. Pat. No. 4,292,270 to Hannah et al., incorporated herein by reference. The distal portion 11 has at least one opening 2 for receiving bodily fluids such as urine once inserted into the urethra or further up into the bladder. The opening 2 may be located at the distal tip or any other part of the distal portion 11 as long as the opening 2 can receive urine once properly positioned. A proximal opening 42 is located at the proximal portion 19, preferably the proximal end. A lumen extends from the distal opening 2 to the proximal opening 42.

The second segment 20 is sometimes termed the "bulbar segment" as it is designed to reside in the bulbar section of the urethra when the prosthesis 9 is placed properly in the patient's urethra. It also has a distal portion 21 and a proximal portion 29. A lumen also extends through the second segment 20 from a distal opening 46 in the distal portion 21, preferably at the distal end, to a proximal opening 48 in the proximal portion, preferably at the proximal end.

The adjustable tie 5 connects the proximal portion 19 of the segment 10 with the distal portion 21 of the segment 20. The tie 5 may be a thread, a ribbon, a cord, a wire, a tape, a line, or the like, that engages, unites, links or holds the two prosthetic segments together. The tie 5 can be made of strands of a polymeric material, of silicone, metal, plastic, or rubber. The tie 5 may also be braided or a monofilament. By adjusting the tie 5, an inter-segmental distance 4 between the proximal portion 19 of segment 10 and the distal portion 21 of segment 20 can be varied. In one embodiment, the adjustable tie 5 is a thread or a medical-grade suture wire that has two ends 6 and 7. The two ends may be tied together or otherwise connected, or not connected at all. The tie 5 may be adjusted through a variety of mechanisms. FIG. 1 illustrates one possible mechanism where the tie 5 forms at least one complete loop between portion 19 and portion 21. More specifically, the tie 5 shown in FIG. 1 forms a one-and-half loop as the two ends 6 and 7 are not connected here. The tie 5 may be of a sufficient length that both ends 6 and 7 extend outside the patient's body when the prosthesis is in use. If the ends 6 and 7 are connected, the tie 5 forms two loops of differing sizes between the portion 19 and portion 21. The smaller loop 14 controls the inter-segmental distance 4 and the larger loop 85 may be partly outside a patient's body for extracorporeal manipulation during use.

In the particular embodiment illustrated in FIG. 1 where the two ends are not connected, pulling both ends 6 and 7 will shrink the smaller loop 14 connecting portion 19 and portion 21, effectively shortening the inter-segmental distance 4. When the two ends are connected at a knot, the inter-segmental distance 4 can similarly be shortened by pulling the knot or both sides of the knot toward the knot. In a preferred compact configuration, the adjustable tie 5 is tightened to its foremost, and the proximal portion of the first segment directly contacts the distal portion of the second segment. The two lumens are in close alignment and the inter-segmental distance 4 essentially becomes null. The inter-segmental distance 4 can also be lengthened. One mechanism to lengthen the distance 4 is shown in FIG. 1, in which at least one retrieval piece 25 is attached to segment 20, preferably to its proximal portion 29, and the smaller loop 14 of the tie 5 is enlarged by pulling the retrieval piece 25 substantially away from the first segment 10. The retrieval piece 25 may be a thread, a ribbon, a wire, a tape, a suture, or the like, and may be made of similar material as the adjustable tie 5.

Figure 6:
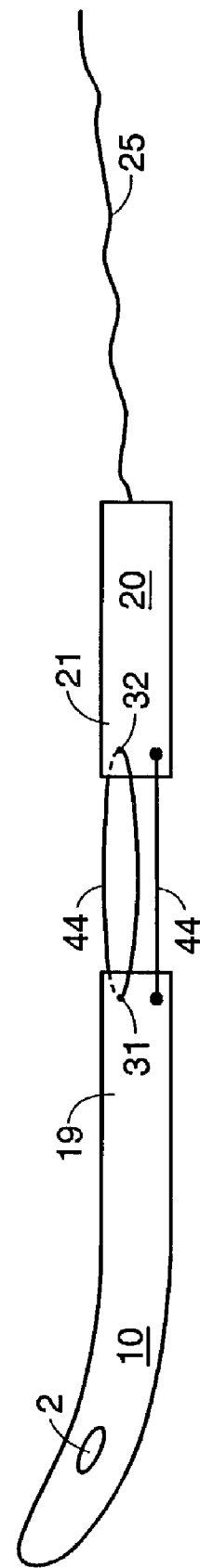
FIG. 6 shows a second and extended configuration of the prosthesis of FIG. 5.

At least one second tie 18 may also connect the proximal portion 19 of the segment 10 and the distal portion 21 of the segment 20. Like the adjustable tie 5, the second tie 18 may be a thread, a ribbon, a cord, a wire, a tape, a line, or the like, that engages, unites, links or holds the two prosthetic segments together. The second tie 18 may also be made of similar materials as the tie 5. The second tie 18 has a pre-determined inter-segmental length, i.e., the length of the second tie 18 between the two prosthetic segments, once the second tie 18 is fully extended, is fixed. In the particular embodiment shown in FIG. 1, the second tie 18 is fixedly fastened to the first segment 10 at point 31, and to the second segment 20 at point 32. Because the second tie 18 is fixedly fastened at both ends in this case, its length between the first and second prosthetic segments 10 and 20, i.e., its inter-segmental length, is pre-determined. When the second tie 18 is fully extended, its inter-segmental length becomes the inter-segmental distance 4. In the particular embodiment shown in FIG. 1, as the segment 20 is pulled away from the segment 10 by the retrieval piece 25, the inter-segmental distance 4 gradually increases until stopped by a fully-extended second tie 18. Therefore, the inter-segmental length of the second tie 18 sets the maximum value for the inter-segmental distance 4. However, the invention also contemplates using other structures known to a skilled artisan to set the maximum value of the inter-segmental distance 4. One example is to use a closed loop between the segments 10 and 20 as shown in FIG. 6 in which the loop engages the two prosthetic segments at points 31 and 32 and the second tie 44 may be able to slide through the points 31 and 32. There may also be multiple adjustable ties 5 and multiple second ties 18 in a prosthesis 9 connecting the two segments 10 and 20.

Figure 2A:
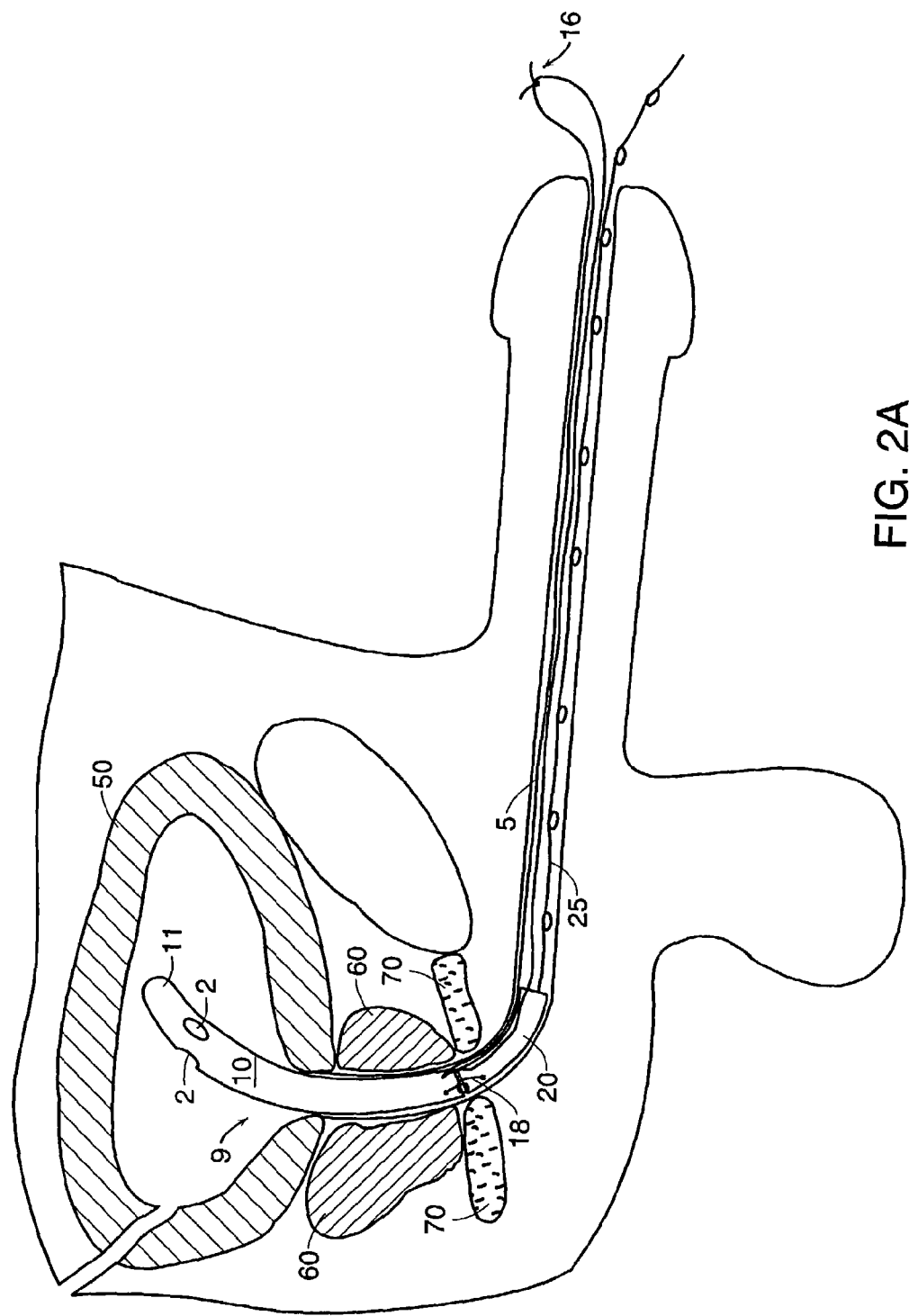
FIG. 2a illustrates the prosthesis of FIG. 1 in a first and compact configuration inside the urethra of a patient.
Figure 2B:
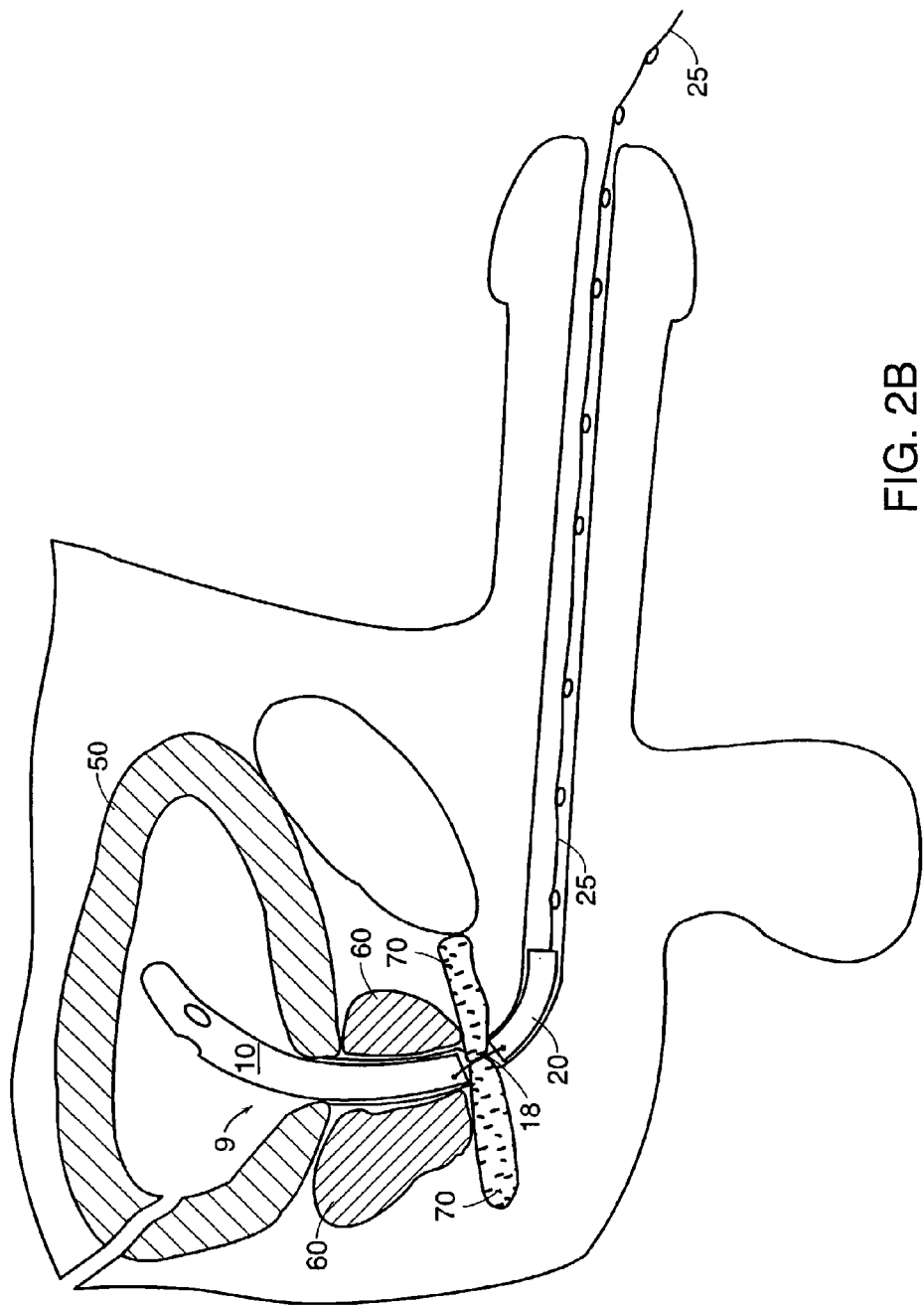
FIG. 2b illustrates the prosthesis of FIG. 1 in a second and extended configuration inside the urethra of a patient.

FIGS. 2a–2b illustrate how the embodiment of FIG. 1 can be used to assist urinary voiding. The prosthesis 9 is inserted, through the penile urethra, further up into the urethra of a patient, until the distal portion 11 of the prostatic segment 10 is disposed in the bladder 50 where the distal opening 2 can receive urine. Proper positioning of the prosthesis can be confirmed through a cystoscope or other means, one of which will be discussed later in association with FIGS. 3–4. Once properly positioned, a portion of the prostatic segment 10 should be inside the prostatic urethra, which is adjacent to a prostate 60. The connection between the prostatic segment 10 and the bulbar segment 20 should be adjacent to an external urinary sphincter 70. When normal sphincter function is compromised, such as when the patient is under anesthesia, the inter-segmental distance 4 between segments 10 and 20 is shortened, through ways described in association with FIG. 1. As particularly shown in FIG. 2a, the adjustable tie 5 connects the first and second segments 10 and 20 of the prosthesis 9 in two loops, as the two ends of the tie 5 are connected at a knot 16. Upon pulling the knot 16 substantially away from the first segment 10, the smaller loop formed by tie 5 gets tightened, bringing the two segments close enough to allow constant fluid communication between their lumens. Under this compact configuration, the prosthesis holds the urethra and the external sphincter muscles 70 open, thereby providing constant urine drainage through the aligned lumens.

When the patient regains voluntary control over the external sphincter 70, such as when the effects of anesthesia wears off, an extended configuration of the prosthesis may be used to allow voluntary control over urine voiding. As shown in FIG. 2b, the inter-segmental distance 4 between the prostatic segment 10 and bulbar segment 20 is lengthened, allowing the insertion of the external sphincter 70. If the prosthesis 9 is in the compact configuration depicted in FIG. 2a, an operator may transform the prosthesis 9 into an extended configuration by increasing the distance between the segments 10 and 20. The operator may pull the retrieval piece 25, attached to the proximal portion of the bulbar segment 20, substantially away from the prostatic segment 10, until stopped by the second tie 18. In this case, the inter-segmental distance 4 increases toward its maximum value set by the second tie 18 that connects the two segments. Since the extended configuration does not rely on the adjustable tie, the adjustable tie may be cut loose, if knotted, and/or removed from the urethra while at least a portion of the prosthesis 9 remains inside the urethra. The removal can be achieved by simply pulling one loose end of the adjustable tie 5 out of the urethra. The rest of the tie 5 will follow. Under this extended configuration, the distance between the prostatic segment 10 and bulbar segment 20 may be designed to be long enough for the sphincter muscles 70 to contract between the two tubular segments and intercept or block fluid flow between the lumens of the segments 10 and 20.

The methods provided here are particularly useful for patients whose external sphincter function is temporarily compromised, as in the situation of undergoing an anesthetic procedure that affects the sphincter muscles. When the sphincter is under the influence of anesthesia, the prosthesis may assume a compact configuration, such as one depicted in FIG. 2a, to provide constant urine drainage. When the effect of anesthesia is wearing off, the prosthesis may be transformed into an extended configuration, such as one depicted in FIG. 2b, to allow voluntary control over urine voiding through the external sphincter. There may be a variety of reasons why the patient needs the assistance of a urinary prosthesis, such as in the situation of having enlarged prostate 60, which obstructs the prostatic urethra. By using a prosthesis described here, the patient has the ability to control assisted voiding as soon as his external sphincter regains its function.

A collecting device such as a condom catheter may be placed around the patient's penis for receiving drained fluid. Since the bulbar segment typically does not extend outside the patient's body, and only the ties and the retrieval piece extend that far, the risk of infection is minimized.

Figure 3:
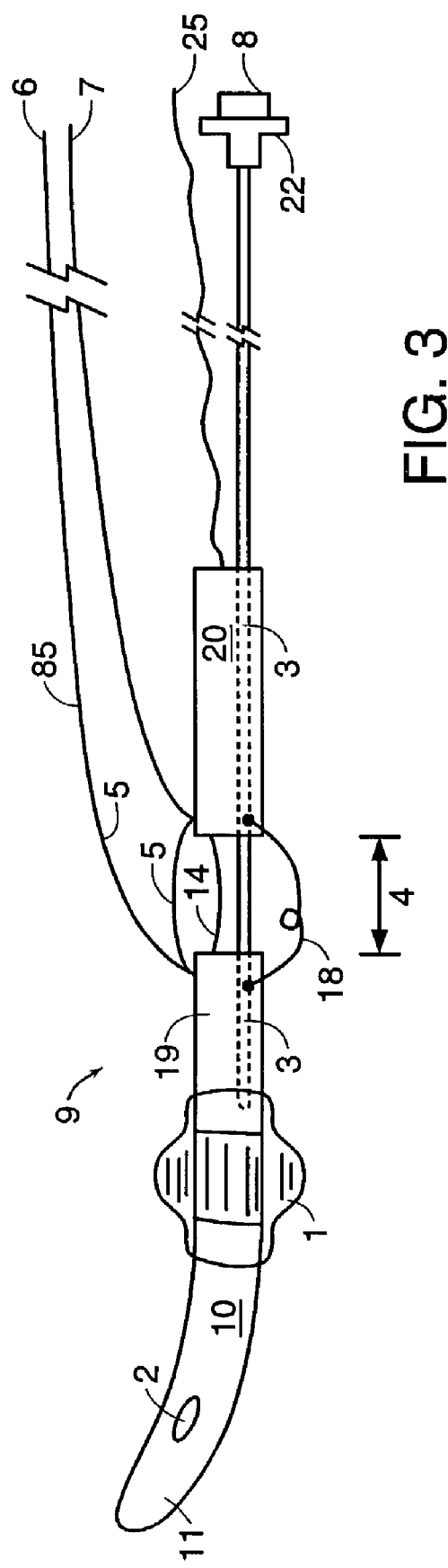
FIG. 3 illustrates certain features of one disclosed embodiment of a urethral prosthesis according to the invention.

FIG. 3 shows some additional features that may be incorporated into various embodiments of the invention. The prostatic segment 10 may include an inflatable balloon 1 connected through a tube 3 to an inflation source 8 that can introduce fluid (e.g., air, saline fluid) into tube 3. The tube 3 may be made of a flexible material. In the particular embodiment shown in FIG. 3, the inflation source is a syringe with a check valve 22. Once the balloon 1 is inflated, the check valve 22 (or a one-way valve) ensures that the balloon stay inflated by stopping fluid from flowing back. Other auxiliary structures, such as a malecot, that can be enlarged from outside the patient's body once the prosthesis is inserted into the urethra are also contemplated to be useful here.

Figure 4:
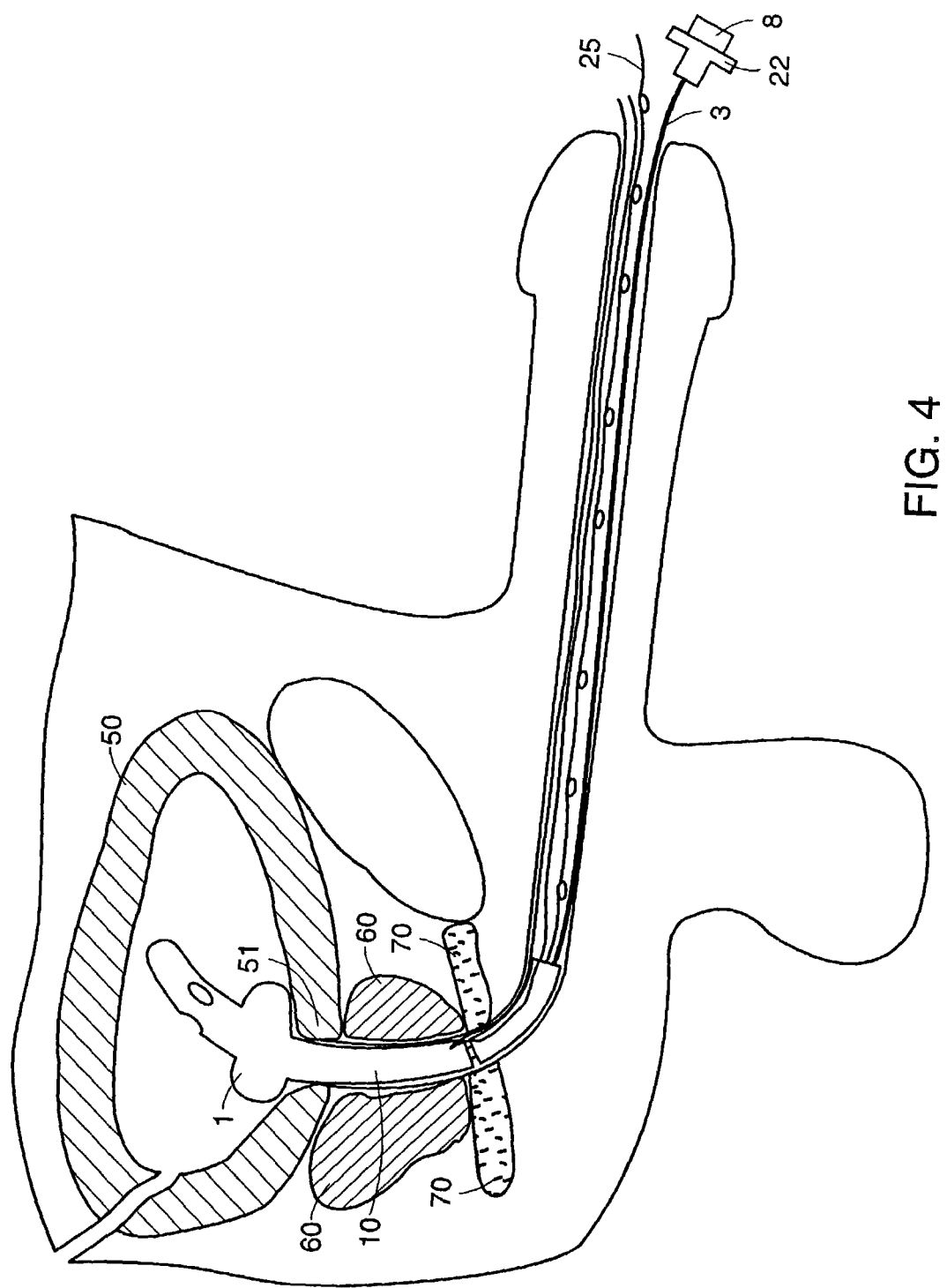
FIG. 4 illustrates a method of using some of the features shown in FIG. 3 to assist placement of a urethral prosthesis inside a patient's urethra.

The balloon or its equivalent structure can be used to confirm proper placement of the prosthesis. Referring to FIG. 4, first, the prosthesis is inserted high up the urethra where the balloon portion most likely enters the bladder 50. Then a volume of fluid is delivered through the tube 3 to inflate the balloon 1. And the operator pulls on the retrieval piece 25 to withdraw the prosthesis until resistance is felt, meaning that the inflated balloon 1 has been stopped by the bladder neck 51. The prosthesis is designed so that the portion from the balloon to the proximal end of the prostatic segment 10 corresponds to the length of the prostatic urethra—once the balloon hits the bladder neck, the connection between the prostatic segment and the bulbar segment is substantially adjacent to the sphincter muscles 70. This means of confirming the proper placement of a urinary prosthesis does not require the use of a cystoscope, permitting a general practitioner or other medical staff to perform this procedure.

A third tubular segment may optionally be attached proximally to the bulbar segment. The third segment contains a lumen aligned with the lumen of the bulbar segment. The third segment may be removably connected to the bulbar segment (e.g. using an adjustable tie similar to the one used to connect the prostatic segment with the bulbar segment). The third segment may be long enough to extend outside the patient's body during use. A drainage bag may be connected to the proximal portion of the prosthesis (e.g., the proximal portion of the third segment) to collect drained fluid.

Figure 5:
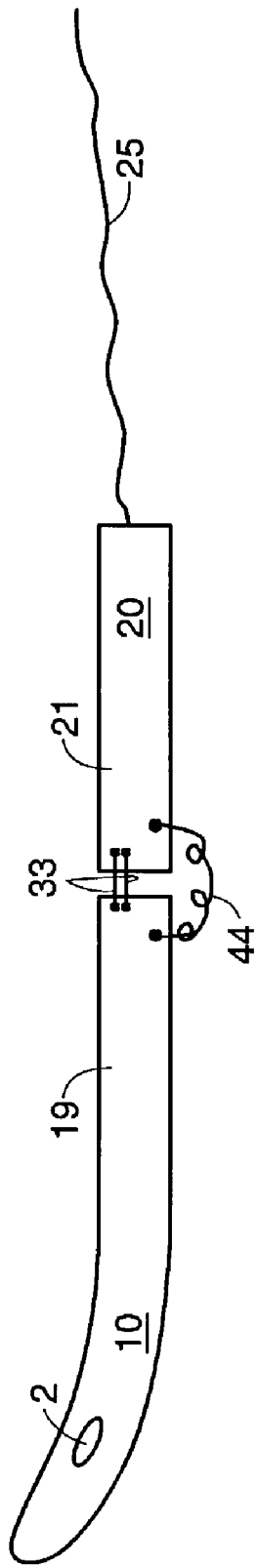
FIG. 5 shows a first and compact configuration of another embodiment of a prosthesis according to the invention.

A further embodiment of the invention is illustrated in FIGS. 5–6. A prostatic segment 10 and a bulbar segment 20 similar to the ones described earlier are connected by at least one first tie 33 and at least one second tie 44. Both ties may be a thread, a ribbon, a cord, a wire, a tape, a line or the like, that engages, unites, links or holds the two prosthetic segments together. The first tie 33 engages the two segments by holding them in close proximity to allow fluid communication between the lumens of the segments 10 and 20. The second tie 44 connects the two segments with a pre-determined inter-segmental length. In a preferred embodiment, the first tie 33 holds the proximal portion 19 of the segment 10 in direct contact with the distal portion 21 of the segment 20. The second tie 44 may be fixedly fastened, at both ends, to the prosthesis, as shown in FIGS. 5–6. Or, as also shown in FIG. 6, the second tie 44 may be a closed loop between the segments 10 and 20, and at points 31 and 32 where the second tie 44 engages the prosthesis, the second tie 44 may be able to slide through the points 31 and 32. If the first tie 33 is disengaged from the prosthesis, as shown in FIG. 6, the segment 10 is connected to the segment 20 at a longer inter-segmental distance that is now limited by the second tie 44.

Figure 7:
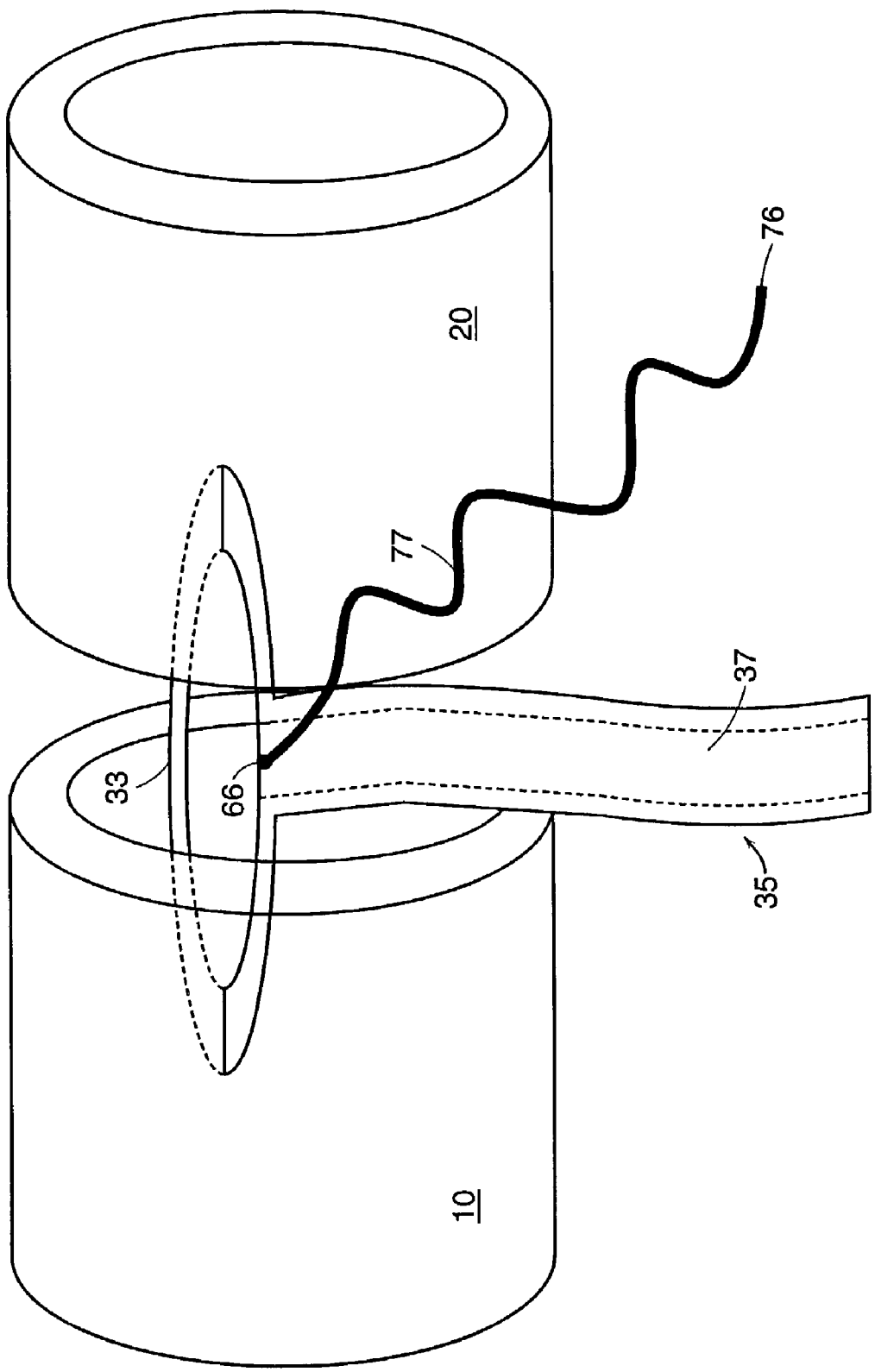
FIG. 7 illustrates an embodiment of a part of the prosthesis shown in FIG. 5.

FIG. 7 illustrates the details of a preferred embodiment of the first tie 33 shown in FIG. 5. The first tie 33 forms a closed loop between the prostatic segment 10 and the bulbar segment 20. At junction 66, a tape portion 35 of the first tie 33 extends out. The junction 66 can adopt a variety of geometric shapes. As shown in FIG. 7, the junction 66 assumes a "T" shape. Alternatively, the junction 66 can adopt a "Y" shape or other suitable shapes. Two perforated lines travel throughout the length of the tape portion 35, dividing the tape portion 35 into three longitudinal sections. A middle section 37 is further connected to an actuation thread 77 at junction 66. The actuation thread 77 may be of a length that, once the prosthesis is properly positioned inside the patient, the thread 77's end 76, which is opposite the junction 66, extends outside the patient's body. When the end 76 of the actuation thread 77 is pulled with enough strength, the perforated lines in the tape portion 35 will tear, starting from junction 66, all the way along the tape portion 35. Consequently, the middle section 37 is torn away, effectively disconnecting the loop formed by the first tie 33. Optionally, the tape section 35 itself may be long enough to extend outside the patient's body during use, and once the loop of the first tie 33 is disconnected at the junction 66 by pulling the actuation read 77, the rest of the loop may be removed from the urethra by simply pulling on the rest of the tape section 35.

To drain bodily fluid from a patient, the embodiment illustrated in FIGS. 5–7 is first inserted into the urethra of a patient. Proper placement may be confirmed, for example, through the inflated balloon in the prostatic segment. The prosthesis may be inserted in a compact configuration where the prostatic segment 10 and the bulbar segment 20 are held close enough, by the first tie 33, to allow fluid communication between the lumens of the prosthesis. In the situation where patient is under anesthesia, the compact configuration provides constant urinary drainage for the patient. When the effect of anesthesia wears off, and the patient regains sphincter function, an operator can pull on the extra-corporeal end 76 of the actuation thread 77, disconnecting the first tie 33 at junction 66, as described above in connection with FIG. 7. Once the first tie 33 is disconnected, the operator may pull on the retrieval piece 25 connected to the proximal portion 29 of the bulbar segment 20 to further separate the two segments into an extended configuration. The second tie 44 now determines the maximum length of the inter-segmental distance, which may be designed to allow the sphincter muscles to contract between the two prosthetic segments and to intercept or block fluid communication between the lumens of the segments.

The invention contemplates the combination of the prosthesis as described above with other auxiliary devices used during treatment or surgical procedure of the urinary tract such as treating urinary retention. The use of the prosthesis may be combined with an insertion sleeve, a pusher, a stylet, an endoscope, and so on. A pusher may be used to advance the prosthesis up the urethra and into the bladder. A stylet may reside within the lumens of both the prostatic segment and the bulbar segment to maintain the overall connection between the segments, especially in the extended configuration.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A prosthesis for insertion into a patient's urethra, comprising:
   (a) a first segment including a distal portion comprising a distal opening, and a proximal portion comprising a proximal opening, the first segment defining a lumen extending therebetween;
   (b) a second segment including a distal portion comprising a distal opening, and a proximal portion comprising a proximal opening, the second segment defining a lumen extending therebetween;
   (c) an operator-adjustable first tie connecting the proximal portion of the first segment and the distal portion of the second segment, the first tie forming at least one loop; and
   (d) a fixed length second tie connecting the proximal portion of the first segment and the distal portion of the second segment.

2. The prosthesis of claim 1, wherein the first tie is adjustable to adopt a compact configuration, positioning the proximal portion of the first segment in direct contact with the distal portion of the second segment.

3. The prosthesis of claim 1, wherein the first tie is adjustable to adopt an extended configuration, in which a distance between the first and second segments permits insertion of an object between the two segments such that the object intercepts fluid communication between the lumens of the first and second segments.

4. The prosthesis of claim 3, wherein the distance between the first and second segments permits operation of an external sphincter muscle.

5. The prosthesis of claim 1, wherein the first tie comprises a thread with two ends.

6. The prosthesis of claim 5, wherein the two ends of the thread are connected.

7. The prosthesis of claim 6, wherein the ends of the thread are knotted together.

8. The prosthesis of claim 6, wherein the length of the second tie sets a maximum value for the distance between the first and second segments.

9. The prosthesis of claim 8, wherein the maximum value for the distance between the first and second segments permits insertion of an object between the two segments such that the object intercepts fluid communication between the lumens of the first and second segments.

10. The prosthesis of claim 9, wherein the maximum value for the distance between the first and second segments permits operation of an external sphincter muscle.

11. The prosthesis of claim 5, wherein the two ends of the thread are not connected.

12. The prosthesis of claim 5, wherein the thread forms a one-and-a-half loop between the proximal portion of the first segment and the distal portion of the second segment.

13. The prosthesis of claim 1, wherein the first segment further comprises an inflatable balloon.

14. The prosthesis of claim 1, wherein the distal portion of the first segment further comprises a coudé tip.

15. The prosthesis of claim 1, wherein the first and second segments comprise a biocompatible material.

16. The prosthesis of claim 15, wherein the biocompatible material comprises silicone.

17. The prosthesis of claim 1, further comprising a retrieval piece connected to the second segment.

18. The prosthesis of claim 17, wherein the retrieval piece comprises a thread.

19. The prosthesis of claim 1, wherein the length of the second tie is less than the length of the first tie.

20. The prosthesis of claim 1, further comprising a first connection aperture located at the proximal portion of the first segment and a second connection aperture located at the distal portion of the second segment.

21. The prosthesis of claim 20, wherein at least one of the first tie and the second tie connects the proximal portion of the first segment and the distal portion of the second segment via the first and second connection apertures.

* * * * *